(12) United States Patent
Tofighbakhsh et al.

(10) Patent No.: US 10,477,261 B2
(45) Date of Patent: Nov. 12, 2019

(54) SENSORY COMMUNICATION SESSIONS OVER A NETWORK

(71) Applicant: AT&T Intellectual Property I, L.P., Atlanta, GA (US)

(72) Inventors: Mostafa Tofighbakhsh, Cupertino, CA (US); David R. Wolter, Austin, TX (US); Milap Vrashank Majmundar, Austin, TX (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 784 days.

(21) Appl. No.: 13/655,994

(22) Filed: Oct. 19, 2012

(65) Prior Publication Data

US 2014/0115092 A1    Apr. 24, 2014

(51) Int. Cl.
| | |
|---|---|
| *H04N 21/414* | (2011.01) |
| *H04L 29/08* | (2006.01) |
| *H04N 21/4788* | (2011.01) |
| *H04N 21/422* | (2011.01) |
| *A61B 5/00* | (2006.01) |
| *A61B 5/01* | (2006.01) |
| *A61B 5/024* | (2006.01) |
| *A61B 5/08* | (2006.01) |
| *A61B 5/11* | (2006.01) |
| *A61B 5/16* | (2006.01) |

(52) U.S. Cl.
CPC ....... *H04N 21/41407* (2013.01); *H04L 67/18* (2013.01); *H04L 67/22* (2013.01); *H04L 67/306* (2013.01); *H04N 21/422* (2013.01); *H04N 21/4788* (2013.01); *A61B 5/01* (2013.01); *A61B 5/024* (2013.01); *A61B 5/0816* (2013.01); *A61B 5/1112* (2013.01); *A61B 5/165* (2013.01); *A61B 5/6887* (2013.01); *A61B 5/6898* (2013.01)

(58) Field of Classification Search
CPC .............................. G06F 15/16; G06Q 50/01
USPC ................... 709/217, 204; 715/764; 345/632
See application file for complete search history.

(56) References Cited

U.S. PATENT DOCUMENTS

| | | | | |
|---|---|---|---|---|
| 5,802,526 | A * | 9/1998 | Fawcett | G06F 3/167 348/14.06 |
| 7,650,425 | B2 * | 1/2010 | Davis | G01D 4/004 709/238 |
| 7,877,208 | B1 * | 1/2011 | Battista | H04L 12/403 701/490 |
| 8,494,507 | B1 * | 7/2013 | Tedesco | A61F 4/00 434/112 |
| 9,520,957 | B2 * | 12/2016 | Ramirez Flores | H04H 60/45 |
| 2006/0073819 | A1 * | 4/2006 | Lowles | H04M 1/6041 455/418 |
| 2008/0153512 | A1 * | 6/2008 | Kale et al. | 455/456.3 |

(Continued)

*Primary Examiner* — Younes Naji
(74) *Attorney, Agent, or Firm* — Hartman & Citrin LLC

(57) ABSTRACT

A method and system for enhanced human to human and human to machine interactions employs a sensory communication session that spans from end user device to end user device across a network. The sensory communication session includes remote sensory application programming interfaces that provide standardized access to applications executing on user communication devices. The sensory communication session enables enhanced interactions with a deeper quality of experience and enables each communicating user to better discern feelings, situation, and other environmental and personal context associated with the other user.

18 Claims, 6 Drawing Sheets

(56) References Cited

U.S. PATENT DOCUMENTS

| | | | |
|---|---|---|---|
| 2009/0300525 A1* | 12/2009 | Jolliff | H04M 1/72544 715/764 |
| 2010/0228768 A1* | 9/2010 | Yamasuge | G06F 16/273 707/769 |
| 2011/0098109 A1* | 4/2011 | Leake | A63F 13/213 463/30 |
| 2011/0133927 A1* | 6/2011 | Humphrey | A62B 9/006 340/539.11 |
| 2012/0179754 A1* | 7/2012 | Nilsson | G06F 8/65 709/204 |
| 2012/0190339 A1* | 7/2012 | Abe | H04W 48/16 455/411 |
| 2012/0215844 A1* | 8/2012 | Ferlez et al. | 709/204 |
| 2013/0009994 A1* | 1/2013 | Hill | G06N 3/006 345/633 |
| 2013/0073995 A1* | 3/2013 | Piantino et al. | 715/764 |
| 2013/0166726 A1* | 6/2013 | Boldyrev | G06Q 50/01 709/224 |
| 2014/0090547 A1* | 4/2014 | Udell, III | G10H 1/0091 84/626 |
| 2014/0092130 A1* | 4/2014 | Anderson | G06F 3/011 345/632 |
| 2015/0288508 A1* | 10/2015 | Wilhelmsson | H04W 72/08 370/280 |

* cited by examiner

SENSORY COMMUNICATION SESSIONS OVER A NETWORK

BACKGROUND

Field of the Disclosure

The present disclosure relates to telecommunications and, more particularly, to network communications that include sensory communication.

Description of the Related Art

Users communicate with one another over network channels using communication devices such as smart phones or other mobile devices. While the communications sessions between the users typically involve audio communications only, in some instances, the communication sessions involve both audio and video communications.

DESCRIPTION OF THE EMBODIMENT(S)

Figure 1:
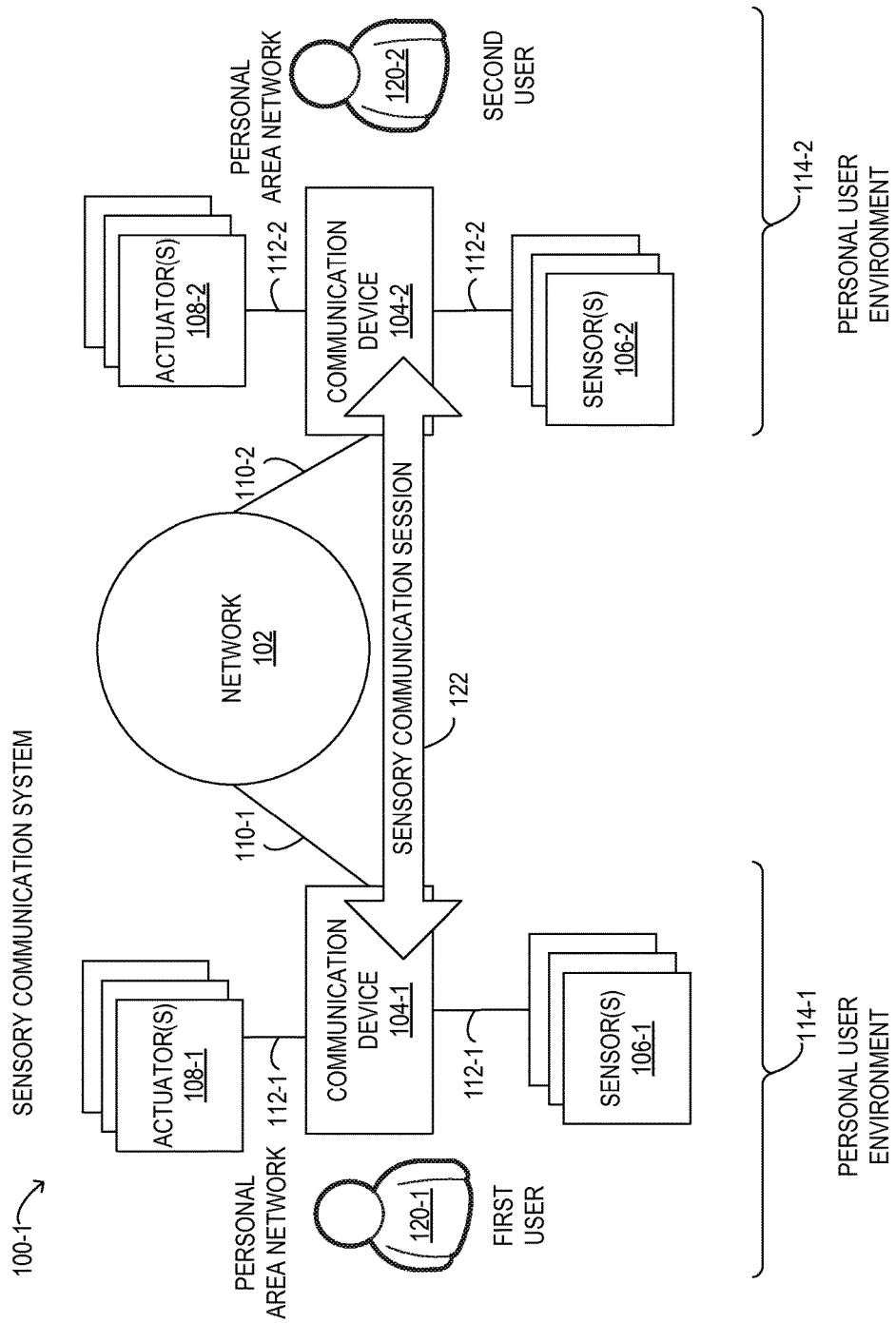
FIG. 1 is a block diagram of selected elements of an embodiment of a sensory communication system.

Many current telecommunication technologies are limited to audiovisual information, such as voice, audio, images, and video. Such technologies may not support the exchange of other detailed information regarding the users participating in the telecommunication session such as historical state information, descriptions of other nearby individuals, environmental information (i.e., temperature, motion (including speed and direction)), and physical/emotional user information.

As will be described in further detail herein, a sensory communication system is disclosed that supports sensory communication sessions between two or more communication devices across a network. The sensory communication session includes support for actuators and sensors that may be associated with the communication devices and/or the users of the communication devices. As used herein, the term users includes both humans and machines. The sensory communication system may obtain sensory information from a first communication device and may provide remote information to present to a second communication device. In this manner, where two users would be interested to see and touch and sense one another via virtual reality applications over a network, the disclosed sensory communication session includes remote sensory application programming interfaces (APIs) and sensor event notification between the source and destinations. The remote sensory APIs and event notifications enable applications to access standardized information, including information such as state, gesture, environment, motion (including speed and direction), location details and background information, and the presence of individuals in the area. The remote sensory APIs may also provide support for discerning moods of the associated users so as to enable proper context sensing and touching initiation between the users.

For example, a source user (A) may want to shake hands with a target user (B) in a virtual environment. Both A and B have opted to share sensory information, such as measurements from local sensors for biometric values, such as body temperature, using the remote sensory APIs. When A's hands are cold, B may be able to remotely recognize A's body temperature during a sensory communication session. With the help of suitable actuators, sensory information may be remotely represented in proxy using remote information provided by the sensory communication session.

In another example, when A is remotely communicating with B over a network, certain environment state and/or device information, such as device battery power status, display capabilities, available sensors, and/or sensor/actuator states may be shared using the sensory communication session. The device information for each party A and B may be presented remotely to the other party in a dashboard along with environmental information such as motion (including speed and direction), geo-location, noise level, ambient conditions, etc. In this manner both A and B may be made aware of state information of the other and changes in the state information during the conversation.

In yet another example, A and/or B may be represented by avatars by the remote communication device. Using remote sensor information for a party, the avatar associated with a party may represent actual features of the party to another party located remotely. Specifically, the avatars may represent size, weight, heart rate, breathing sounds, or moods, as examples, of their respective associated users. The sensor information used for an avatar representation may be available to a user communication device from a sync server. The avatars may thus remotely represent information that has been collected at a user communication device and synched using the remote sensory APIs via the network. In this manner, the sensory communication session may collect remote state information of a user's physical state and device settings for purposes of virtual touch and interaction with another person over a network.

Additionally, the remote sensory APIs may provide user information, such as gesture, directions, agility, movements, facial impressions, and historical intelligence to a communicating party in the form of explicit signals, triggers, and/or event changes. The remote situational states may enable a source to make appropriate presentation of a local environment to a remote counterparty, and may enable, for example, the exchange of appropriate touch and sense signals, in addition to voice and video calling. In some instances, the remote situational states may permit a party to determine the current environmental state of a counterparty, for example mood of the counterparty, so as to permit the party to determine whether to terminate the communication session with the counterparty, including terminating the communication session prior to the counterparty or other user entering into the communication session. In other instances, historical information associated with a user may be analyzed in order to predict the current state of the user (e.g., user recently left a restaurant, and thus, is not hungry; user's motion for the immediately preceding time period indicated an average speed of 45 mph, and thus, the user was recently in a car, etc.). In this manner, the sensory communication session may enable enhanced interactions by enabling each communicating party to better discern feelings, situation, and other environmental and personal context associated with the other party.

In one aspect, a disclosed method for providing a sensory communication session over a network includes determining first sensory information associated with a first user of a first communication device and second sensory information associated with a second user of a second communication device. The method may include identifying, using the first sensory information and the second sensory information, historical sensory data associated with each of the first user and the second user. At a network server, first analytical results and second analytical results using the historical sensory data may be generated. First remote information and second remote information may be generated for presentation at the second communication device and the first communication device, respectively. The first remote information may include the first sensory information and first analytical results for the first user. The second remote information may include the second sensory information and second analytical results for the second user. The first user and the second user may be enabled to discern from the second remote information and the first remote information, respectively, communication session information selected from a group consisting of: environmental information describing a personal user environment, location information for the personal user environment, communication device information, and user information.

In some embodiments, the method may include opening the sensory communication session over the network between the first communication device and the second communication device, discovering active sensors and active actuators configured at the first communication device, and configuring the sensory communication session to support the active sensors and the active actuators. The first analytical results may include estimations of future sensory information for the first user based upon the historical sensory data for the first user. The first remote information may include an avatar display representing the first user and an avatar environment representing a first personal user environment.

In certain implementations, the method further includes synchronizing, at a network server, the first sensory information with the first communication device and the second sensory information with the second communication device. The method may include sending, from the network server, the first remote information to the second communication device and the second remote information to the first communication device. The method may further include enabling the second user to determine whether to terminate the sensory communication session before communicating with the first user based upon the second remote information.

In another aspect, a disclosed network server for enabling a sensory communication session includes a processor configured to access memory media. The memory media includes processor executable instructions to determine first sensory information associated with a first user of a first communication device. The memory media may also include processor executable instructions to identify, using the first sensory information, historical sensory data associated with the first communication device, generate first analytical results using the first historical sensory data, and generate first remote information for presentation at the second communication device, wherein the first remote information includes the first sensory information and the first analytical results. In certain embodiments, the memory media may include processor executable instructions to send the first remote information to the second communication device.

In certain embodiments, the instructions to determine the first sensory information include instructions to establish the sensory communication session between the first communication device and the second communication device. The memory media may include processor executable instructions to synchronize the first sensory information with the first communication device, record the first sensory information to the historical sensory data, wherein the first sensory information is indexed to the first user, and send the second remote information to the first communication device. The processor instructions to synchronize the first sensory information with the first communication device may include updating a sensory profile for the first user. The memory media may include processor executable instructions to synchronize the second sensory information with the second communication device, while a remote sensory programming interface specified by the sensory communication session is used. The processor instructions to send the second remote information to the first communication device are configured to use the remote sensory programming interface. The second communication device may include a sensory machine interface. The second remote information may include second analytical results generated from the historical sensory data for the second communication device. The first sensory information may include information selected from a group consisting of: environmental information describing a personal user environment, location information for the personal user environment, communication device information, and user information.

In a further aspect, disclosed tangible, non-transitory computer readable media include processor executable instructions for implementing a sensory communication session over a network. The instructions may be executable to determine first sensory information associated with a first communication device and second sensory information associated with a second communication device, and identify, using the first sensory information and the second sensory information, historical sensory data associated with each of the first communication device and the second communication device. The instructions may also be executable to generate, at a network server, first remote information and second remote information for presentation at the second communication device and the first communication device, respectively. The first remote information may include the first sensory information and first analytical results generated using the historical sensory data, wherein the first analytical results include estimations of future sensory information for the first communication device. The second remote information may include the second sensory information and second analytical results generated from the historical sensory data. The first communication device and the second communication device may be enabled to present, using the first remote information and the second remote information, communication session information selected from a group consisting of: environmental information describing a personal user environment, location information for the personal user environment, communication device information, and user information for users associated with the first communication device and the second communication device, respectively. The instructions may also be executable to establish the sensory communication session between the first communication device and the second communication device via the network and to synchronize the first sensory information with the first communication device, to synchronize the second communication information with the second communication device, to collect the first sensory information and second sensory information as historical sensory data, to send the first remote information to the second communication device, and to send the second remote information to the first communication device.

In the following description, details are set forth by way of example to facilitate discussion of the disclosed subject matter. It should be apparent to a person of ordinary skill in the field, however, that the disclosed embodiments are exemplary and not exhaustive of all possible embodiments.

Throughout this disclosure, a hyphenated form of a reference numeral refers to a specific instance of an element and the un-hyphenated form of the reference numeral refers to the element generically or collectively. Thus, for example, widget 12-1 refers to an instance of a widget class, which may be referred to collectively as widgets 12 and any one of which may be referred to generically as a widget 12.

Referring to FIG. 1, a block diagram of selected elements of an embodiment of sensory communication system 100-1 is illustrated. In FIG. 1, communication system 100-1 includes network 102, which enables communication devices 104 to establish sensory communication session 122 via links 110, as will be described in further detail. As shown, network 102 and links 110 may represent a public network and/or a private network, such as the Internet or a proprietary network offered by a service provider. Network 102 and links 110 may include various combinations of wired networks and/or wireless networks, which may depend on a given configuration of sensory communication system 100-1. In one embodiment, when communication device 104-1 is a mobile device, link 110-1 may represent a wireless network link, such as a wireless wide area network or a cellular network, while link 110-2 may be a wired network when communication device 104-2 is a personal computer. In other embodiments, communication device 104-2 may be a mobile device, such as a wireless telephony device, while link 110-2 is a wireless network link.

As shown in FIG. 1, sensory communication session 122 may enable exchange of sensory information between personal user environments 114-1 and 114-2, which represent end user network environments for first user 120-1 and second user 120-2 associated with communication device 104-1 and communication device 104-2, respectively. In some embodiments, personal user environments 114 may themselves be mobile. In certain embodiments, personal user environment 114 includes personal area network 112 that enables user 120 to interconnect various local devices. In one embodiment personal area network 112 may be a Bluetooth® link. In various embodiments, personal area network 112 may include wireless networks, such as IEEE 802.11 (WiFi). For example, communication device 104-1 may be networked via personal area network 112-1 to actuators 108-1 and/or sensors 106-1 in personal user environment 114-1 associated with first user 120-1. In this example, personal area network 112-1 may be a wired and/or wireless network. Actuators 108 may represent, for example, any of a variety of electronic, electro-mechanical and/or electro-chemical devices that convert physical stimuli, such as motion, pressure, force, temperature, vibration, etc. to electrical signals and/or data. Actuators 108 may also include interfacing components (not shown) for communication via personal area network 112. Sensors 106 may represent any of a number of sensing devices for conversion of physical stimuli, including motion, pressure, force, temperature, vibration, etc., to electrical signals and/or data. As shown in FIG. 1, personal user environment 114 may include various numbers and configurations of actuators 108 and/or sensors 106. In certain instances, personal user environment 114 may be operated without actuators 108 and/or sensors 106. It is also noted that communication device 104 may itself include (or be equipped with) various sensors and/or actuators (not shown), such as imaging devices, lighting elements, microphones, loudspeakers, projectors, touch sensors, haptic actuators, gyroscopes, global positioning system receivers, etc. As shown in FIG. 1, personal user environment 114-2 may correspondingly include personal area network 112-2, which networks actuators 108-2 and/or sensors 106-2 to communication device 104-2 usable by second user 120-2.

In operation of communication system 100-1, sensory communication session 122 enables first user 120-1 to communicate with second user 120-2 while supporting the use of actuators 108 and sensors 106 to add sensory information to a communication channel and thereby enhancing the communication experience of first user 120-1 and second user 120-2.

Figure 2:
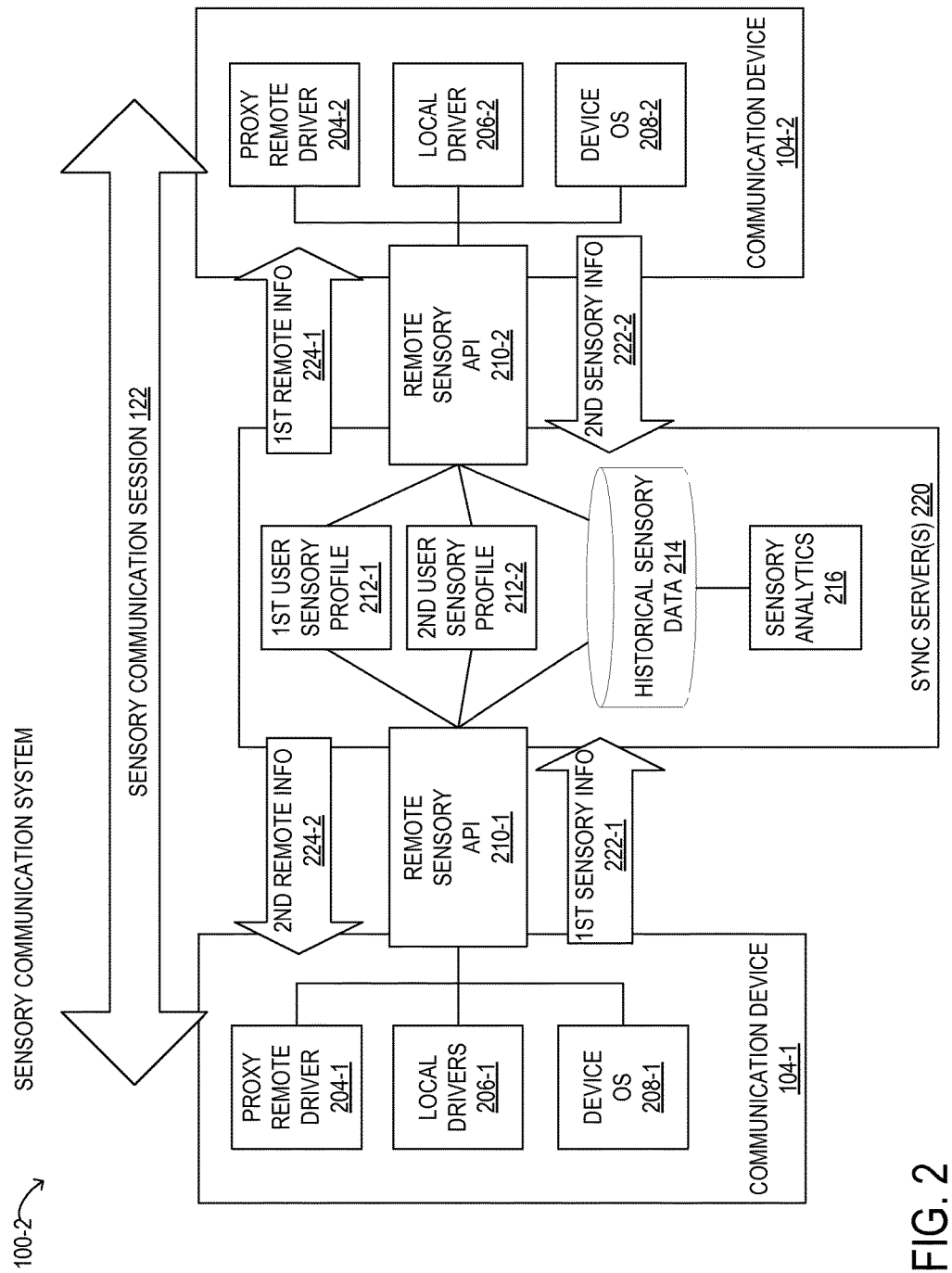
FIG. 2 is a block diagram of selected elements of an embodiment of a sensory communication system.

Turning now to FIG. 2, a block diagram of selected elements of an embodiment of sensory communication system 100-2 is illustrated. Sensory communication system 100-2 represents another view of sensory communication system 100-1 (see FIG. 1) with additional structural and functional elements. In particular, in sensory communication system 100-2, sensory communication session 122 spans from communication device 104-1 to communication device 104-2, representing the endpoints of a communication channel and illustrating various components and interfaces of sensory communication session 122, as will now be described in further detail.

In FIG. 2, sensory communication system 100-2 includes sensory communication session 122, which spans from communication device 104-1 to communication device 104-2 via sync server 220, representing data processing capacity of a network (not shown in FIG. 2, see network 102 in FIG. 1) linking communication devices 104. Sync server 220 may provide network support for a plurality of communication devices 104. In this manner, communication device 104 may only need to make a connection with sync server 220 to enjoy many features provided by sensory communication session 122. Although two communication endpoints (i.e., communication devices 104) are shown in FIGS. 1 and 2 to illustrate a point-to-point communication channel between two parties with descriptive clarity, it will be understood that, in different embodiments, sensory communication session 122 may support multiple communication endpoints and a plurality of channels.

In sensory communication system 100-2, communication devices 104 are shown including proxy remote driver 204, local drivers 206, and device operating system (OS) 208. Proxy remote driver 204 may be configured to receive remote information 224 describing a state of a remote sensor of a communicating user and provide remote information 224 at communication device 104. In contrast, local drivers 206 may be configured to provide a software interface for local sensors and actuators (see, e.g., sensors 106, actuators 108 in FIG. 1) and compatibility with device OS 208, thereby generating sensory information 222. Device OS 208 may represent an operating system installed and executing on communication device 104. For example, device OS 208 may be a UNIX or UNIX-like operating system, a Windows® family operating system, or another suitable operating system. In certain embodiments, when communication device 104 is a mobile device, such as a wireless telephone device, device OS 208 may be an Android™ operating system (Google, Inc.) or an iOS™ operating system (Apple Corp.).

Also shown in FIG. 2 is remote sensory API 210, representing standardized routines and functions that may be accessed by local applications (not shown) to send and receive sensory information 222 and remote information 224 to/from communication devices 104. Remote sensory API 210 may be usable to access remote information 224 and sensory information 222 from sync server 220, as well as to collect sensory information 222 and generate remote information 224 at sync server 220. Sensory information 222 and/or remote information 224 may include various types of information that users may be able to discern, including (but not limited to): environmental information describing personal user environment; location information for the personal user environment; communication device information; and user information for users associated with communication devices 104. In various embodiments, remote information 224 and sensory information 222 may be organized as data elements comprising individual values, also referred to as tag values or tags.

Tag values may comprise a time-stamped value determined by a sensor or an actuator or a manually entered value. Environmental information may include first tag values describing lighting conditions, ambient temperature, weather conditions, ambient pressure, ambient noise levels, an indoor environment, an outdoor environment, an in-vehicle environment, individuals in an environment, events occurring in an environment, or a combination thereof. Location information may include second tag values describing: a geographical position, a speed, an acceleration, a direction, a sea level elevation, a destination, an estimated travel time, an estimated arrival time, a premises descriptor, a physical address, an entity name, a property owner, or a combination thereof. Communication device information may include third tag values describing: a device type, a device model, a device manufacturer, a software vendor, a sensor type, an actuator type, a device interface, display or presentation information, power information, a peripheral interface, an operating system, an operating condition, a sensor value, an actuator value, or a combination thereof. User information may include fourth tag values describing: a gesture, a facial expression, a mood, biometric information, a health condition, a hairstyle, a clothing style, a skin feature, medical information, or a combination thereof.

In FIG. 2, sync server 220 is shown including user sensory profiles 212, historical sensory data 214, and sensory analytics 216. User sensory profiles 212 may represent user information for particular users, including user preferences and other parameters used by sensory communication session 122, that is stored at sync server 220. Historical sensory data 214 may store historical logs of sensory information 222 and other information for particular users. Sensory analytics 216 may represent an intelligent module that accesses user sensory profiles 212 as well as historical sensory data 214 to generate remote information 224.

In operation, a first user (not shown in FIG. 2, see first user 120-1 in FIG. 1) operates communication device 104-1 executing device OS 208-1 while a second user (not shown in FIG. 2, see second user 120-2 in FIG. 1) operates communication device 104-2 executing device OS 208-2. It is noted that device OS 208-1 may be a different operating system than device OS 208-2. Local drivers 206-1 interface with local sensors and actuators at communication device 104-1, while local drivers 206-2 interface with local sensors and actuators at communication device 104-2. Local drivers 206 generate respective sensory information 222 based on whichever local sensors and actuators are in use at communication device 104. Accordingly, communication device 104-1 generates and delivers first sensory information 222-1 to sync server 220 using remote sensory API 210-1, while communication device 104-2 may generate and deliver second sensory information 222-2 to sync server 220 using remote sensory API 210-2. Sync server 220 receives sensory information 222 from communication devices 104 and may employ sensory analytics 216, user sensory profiles 212, and historical sensory data 214 to generate remote information 224. So for example, sync server 220 may provide $1^{st}$ remote information 224-1, which includes at least some of $1^{st}$ sensory information 222-1, to proxy remote driver 204-2 at communication device 104-2. Conversely, sync server 220 may provide $2^{nd}$ remote information 224-2, which includes at least some of 2nd sensory information 222-2, to proxy remote driver 204-1 at communication device 104-1. Additionally, sync server 220 may populate $1^{st}$ user sensory profile 212-1 with user settings and/or portions of $1^{st}$ remote information 224-1, and may populate $2^{nd}$ user sensory profile 212-2 with user settings and/or portions of 2nd remote information 224-2. Certain portions of sensory information 222 may also be recorded by sync server 220 in historical sensory data 214. It is noted that remote sensory API 210-1 and 210-2 may represent separate instances from the same set of programming interfaces.

In sensory communication system 100-2 shown in FIG. 2, proxy remote driver 204-2 may receive $1^{st}$ remote information 224-1 and use $1^{st}$ remote information 224-1 to present representations of $1^{st}$ sensory information 222-1 at communication device 104-2, without having to directly interface with communication device 104-1. Similarly, proxy remote driver 204-1 may receive 2nd remote information 224-2 and use 2nd remote information 224-2 to present representations of 2nd sensory information 222-2 at communication device 104-1, without having to directly interface with communication device 104-2. In this manner, sensory communication session 122 may enable the standardized exchange of sensory information between communicating parties without having detailed knowledge of particular details of hardware and/or software implementations at any communication endpoint. In different embodiments, sensory communication session 122 provides remote sensory APIs 210 to applications that target communication devices 104. It is noted that in certain embodiments, sensory communication system 100 may be provided as a service on a new and/or existing network platform. For example, consumers may be provided a choice of experiencing sensory communication sessions 122 as an add-on feature or brand label that certifies certain applications, device OSs 208, and/or communication devices 104.

Figure 3:
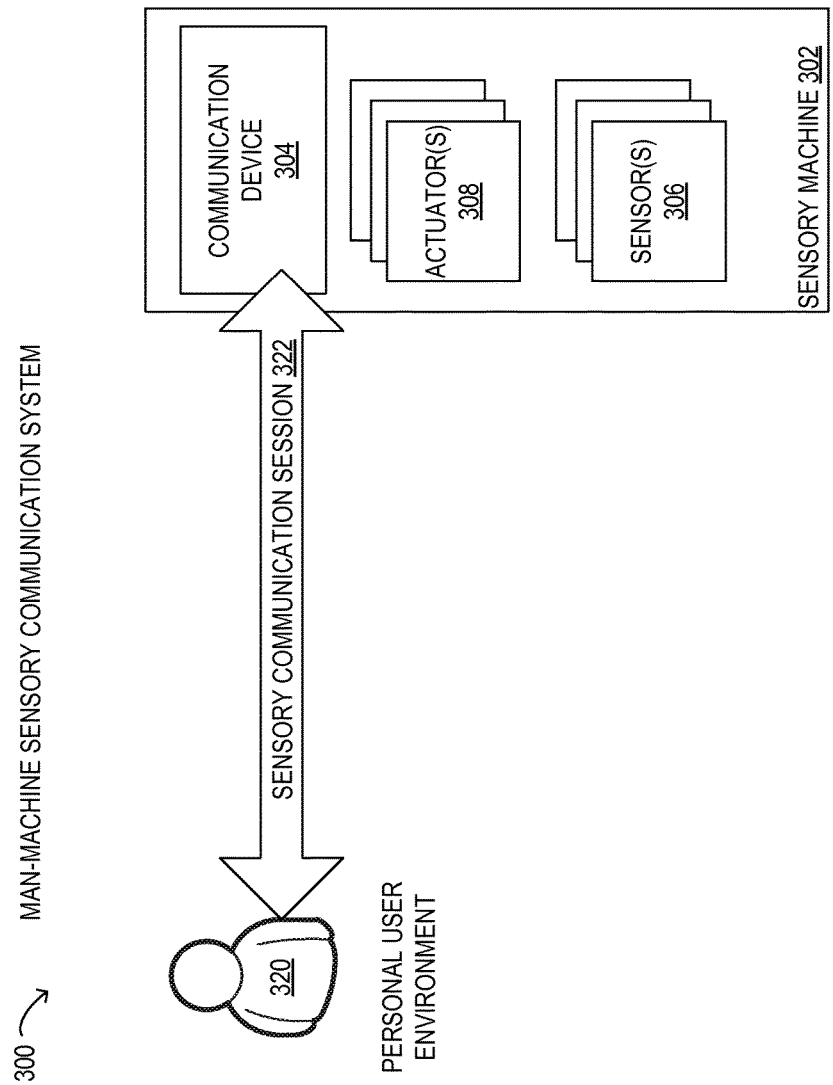
FIG. 3 is a block diagram of selected elements of an embodiment of a man-machine sensory communication system.

Advancing now to FIG. 3, a block diagram of selected elements of an embodiment of sensory communication system 300 is illustrated. As shown, sensory communication system 300 depicts an embodiment in which a user, represented by personal user environment 320, communicates with sensory machine 302 using sensory communication session 322, which may also be referred to as a man-machine interface herein. In sensory communication system 300, personal user environment 320 may be similar to personal user environment 114 (see FIG. 1) associated with user 120, as described previously.

In FIG. 3, sensory machine 302 may represent an automated communicating party or user that is compatible with sensory communication session 322. As shown, sensory machine 302 includes communication device 304, which may represent an embedded version of communication device 104 (see FIGS. 1, 2) that is machine-controlled but with similar functionality. Sensory machine 302 is also shown including actuators 308 and sensors 306, which may be similar to actuators 108 and actuators 106 (see FIG. 1), but are suitable for embedded and/or automated use. Sensory machine 302 may represent any of a number of machine embodiments in applications such as medicine, transportation, military/security, or manufacturing, among others. In one exemplary embodiment, sensory machine 302 may be an autonomous vehicle under control from personal user environment 320, while sensory communication session 322 enables exchange of enhanced feedback, such as steering feel, vibration, pitch, roll, or acceleration, along with various vehicle parameters. In another exemplary embodiment, sensory machine 302 may be a service robot for caretaking, such as in a hospital, clinic, nursing home, etc., while sensory communication session 322 enables realistic human-like response and interaction from a remote user at personal user environment 320 with individuals interacting with sensory machine 302. Other man-machine embodiments of sensory communication system 300 may also be implemented.

Figure 4:
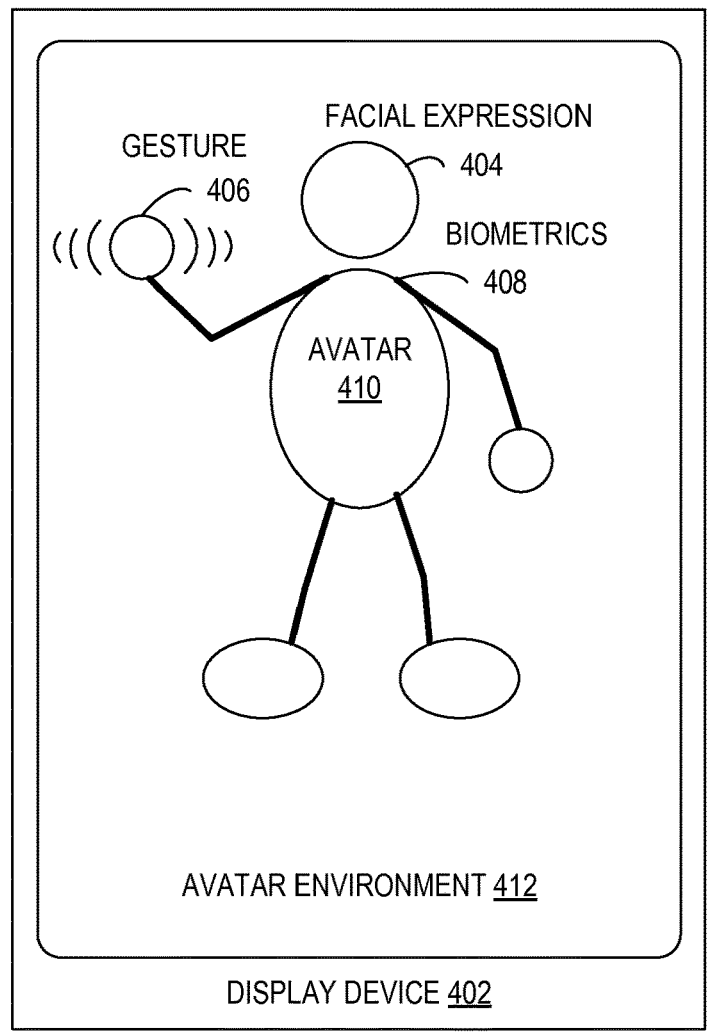
FIG. 4 is a block diagram of selected elements of an embodiment of a sensory avatar display.

Referring now to FIG. 4, a block diagram of selected elements of an embodiment of sensory avatar display 400 is illustrated. As shown, sensory avatar display 400 depicts avatar environment 412 being displayed on display device 402. Display device 402 may be implemented as a liquid crystal display screen, a computer monitor, a television, a mobile device display or the like. Display device 402 may comply with a display standard for the corresponding type of display. Standards for computer monitors include analog standards such as VGA, XGA, etc., or digital standards such as DVI, HDMI, among others. A television display may comply with standards such as National Television System Committee (NTSC), Phase Alternating Line (PAL), or another suitable standard. In particular embodiments, display device 402 may be coupled to and/or integrated with communication device 104 (see FIG. 1).

In FIG. 4, avatar environment 412 may depict an avatar representation of a remote communicating party or user using sensory communication session 122 (see FIG. 1) over a network channel. Accordingly, avatar environment 412 may depict various types of sensory information and/or remote information received at display device 402, as described above with respect to FIGS. 1-3. Specifically, avatar environment 412 may include gesture 406, facial expression 404, and biometrics 408 for the remote communicating party, represented by avatar 410. Gesture 406 and facial expression 404 may be computer-generated or may reflect actual movements, mood, behavior, etc. of the remote communicating party that have been captured and transmitted via sensory communication session 122 (not shown in FIG. 3). Biometrics 408 may include various physical and/or physiological signals and associated measurement values for the remote communicating party that are presented using avatar 410. In this manner, sensory avatar display 400 may provide a more realistic and detailed representation of the remote communicating party using sensory information than when only audiovisual information is used. In some embodiments, avatar environment 412 may represent a personal user environment for a remote communicating party.

Figure 5:
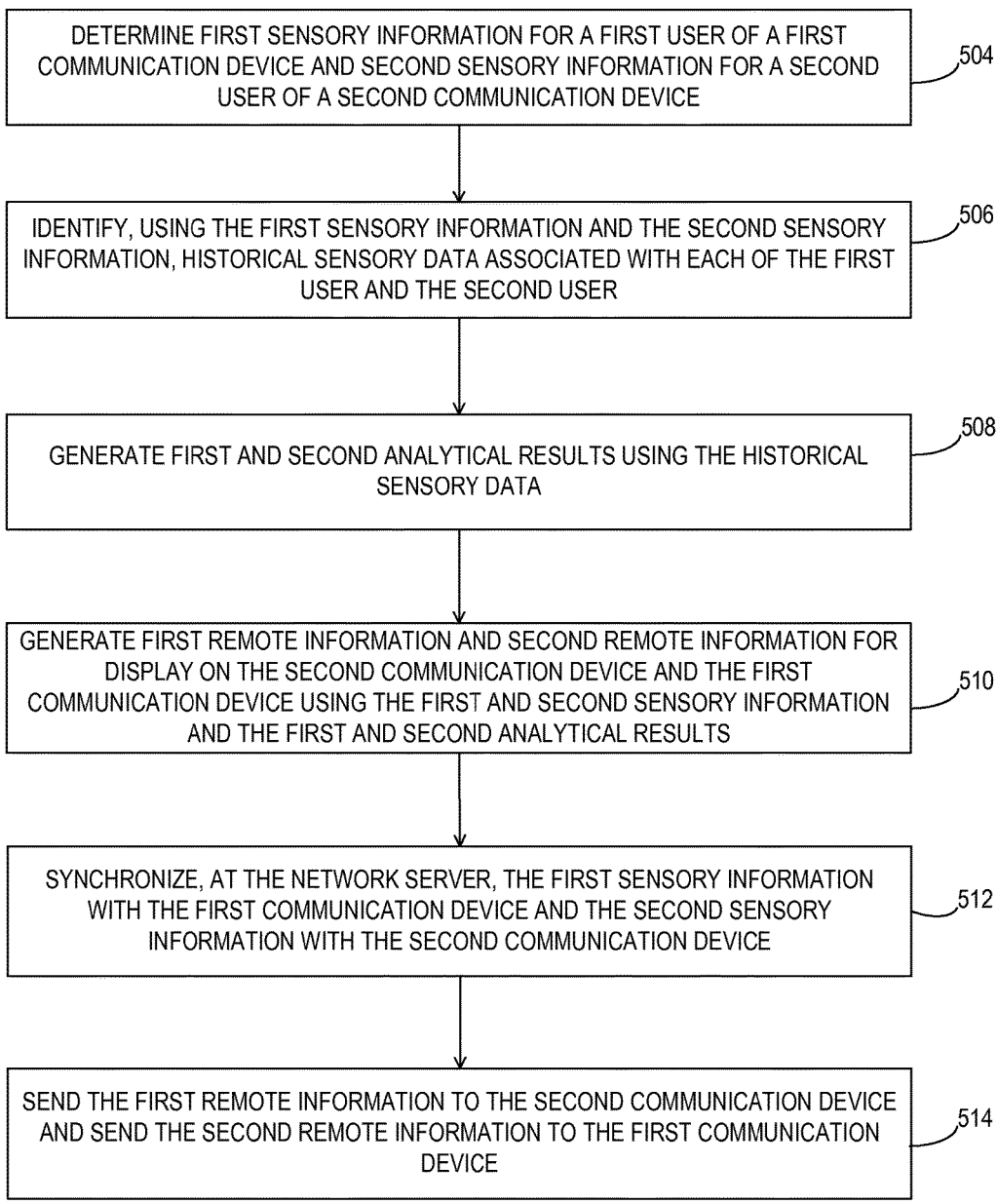
FIG. 5 is a flow diagram of selected elements of a method for implementing a sensory communication session.

Turning now to FIG. 5, an embodiment of method 500 for implementing a sensory communication session is illustrated. In one embodiment, any or all of method 500 is performed by sync server 220 (see FIG. 2). It is noted that certain operations described in method 500 may be optional or may be rearranged in different embodiments. In certain embodiments, it may be assumed that a sensory communication session has been established between a first user and a second user when method 500 is performed. It is also noted that at least certain portions of remote information and sensory information may be recorded by sync server 220 as historical sensory data 214 (see FIG. 2) while method 500 is performed.

Method 500 may begin by determining (operation 504) first sensory information for a first user of a first communication device and second sensory information for a second user of a second communication device. Using the first sensory information and the second sensory information, historical sensory data associated with each of the first user and the second user is identified (operation 506). First analytical results and second analytical results using the historical sensory data may be generated (operation 508). Generation of the first analytical results and the second analytical results may take place at a network server. First remote information and second remote information may be generated (operation 510) for presentation at the second communication device and the first communication device using the first and second sensory information and the first and second analytical results. In given embodiments, the analytical results can include estimations of future sensory information for a respective communication device. At the network server, the first sensory information can be synchronized (operation 512) with the first communication device and the second sensory information can be synchronized (operation 512) with the second communication device. Synchronizing sensory information in operation 512 can include updating a sensory profile for a corresponding user. Synchronizing sensory information in operation 512 may use remote sensory API 210. The first remote information may be sent (operation 514) to the second communication device and the second remote information may be sent (operation 514) to the first communication device.

Figure 6:
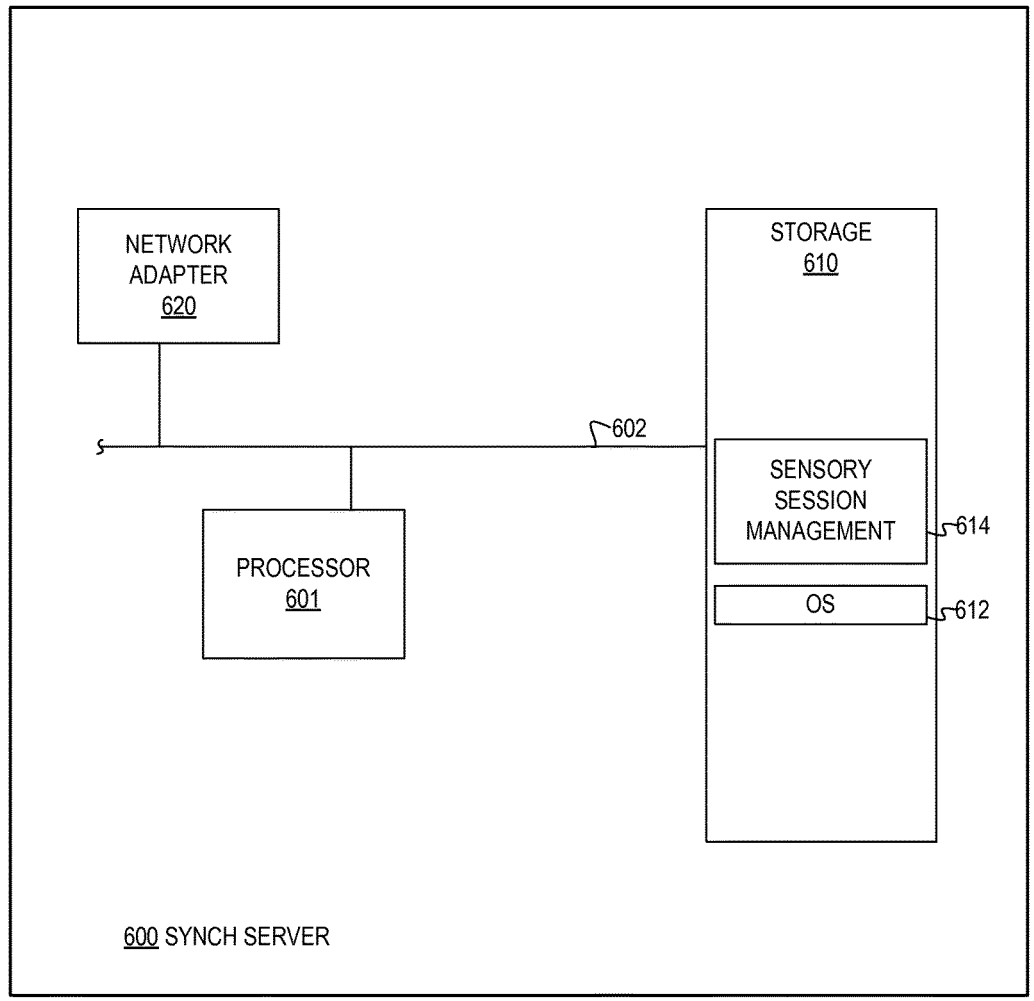
FIG. 6 is a block diagram of selected elements of an embodiment of a computing device.

Referring now to FIG. 6, a block diagram illustrating selected elements of an embodiment of a synch server 600 is presented. In the embodiment depicted in FIG. 6, synch server 600 includes processor 601 coupled via shared bus 602 to storage media collectively identified as storage 610.

Synch server 600, as depicted in FIG. 6, further includes network adapter 620 that interfaces synch server 600 to a network (not shown in FIG. 6). In embodiments suitable for use in sensory network communication, synch server 600, as depicted in FIG. 6, may include other elements, such as a peripheral adapter (not shown) that provides connectivity for the use of input devices and/or output devices. Synch server 600 may also include a display adapter (not shown) and may further include a display device.

Storage 610 encompasses persistent and volatile media, fixed and removable media, and magnetic and semiconductor media. Storage 610 is operable to store instructions, data, or both. Storage 610 as shown includes sets or sequences of instructions, namely, an operating system 612, and sensory session management 614. Operating system 612 may be a UNIX or UNIX-like operating system, a Windows® family operating system, or another suitable operating system. Sensory session management 614 may represent a number of applications and software services for providing sensory communication session 122 and 322 (see FIGS. 1-3), as described herein.

To the maximum extent allowed by law, the scope of the present disclosure is to be determined by the broadest permissible interpretation of the following claims and their equivalents, and shall not be restricted or limited to the specific embodiments described in the foregoing detailed description.

What is claimed is:

1. A method comprising:

establishing, by a sync server of a network, a sensory communication session between a first mobile device associated with a first user and a second mobile device associated with a second user, wherein the sensory communication session comprises a first connection between the sync server and the first mobile device and a second connection between the sync server and the second mobile device, and wherein the first user is associated with a first personal user environment comprising the first mobile device and at least one sensor networked with the first mobile device, and wherein the second user is associated with a second personal user environment comprising the second mobile device and at least one sensor networked with the second mobile device;

discovering, by the sync server, the at least one sensor networked with the first mobile device;

configuring, by the sync server, the sensory communication session to support the at least one sensor networked with the first mobile device;

receiving, by the sync server, via the first connection of the sensory communication session between the sync server and the first mobile device, sensory information from the first mobile device, wherein the sensory information comprises data received from the at least one sensor networked with the first mobile device;

generating, by the sync server, remote information, wherein the remote information is generated by the sync server using the sensory information received from the first mobile device, historical sensory data associated with the first user, and data from a user sensory profile associated with the first user, wherein the remote information comprises at least a portion of the sensory information received from the first mobile device, wherein the remote information further comprises an avatar display generated by the sync server and an avatar environment generated by the sync server, and wherein the avatar display represents the first user and the avatar environment represents the first personal user environment associated with the first user; and providing, by the sync server, via the second connection of the sensory communication session between the sync server and the second mobile device without the first mobile device and the second mobile device directly interfacing with one another, the remote information comprising at least the portion of the sensory information received from the first mobile device, the avatar display generated by the sync server, and the avatar environment generated by the sync server to the second mobile device for presentation by the second mobile device.

2. The method of claim 1, wherein the data received from the at least one sensor networked with the first mobile device comprises environmental information indicative of a current ambient condition at a location of the first mobile device, a lighting condition associated with the location of the first mobile device, and an ambient noise level associated with the location of the first mobile device.

3. The method of claim 1, further comprising estimating a current state of the first user based, at least in part, upon the historical sensory data associated with the first user, wherein the historical sensory data associated with the first user is identified based, at least in part, upon the sensory information received from the first mobile device.

4. The method of claim 1, wherein the sensory information further comprises communication device information associated with the first mobile device and user information associated with the first user.

5. The method of claim 1, wherein the sensory information comprises at least one of a sensor value associated with the at least one sensor networked with the first mobile device or a sensor type associated with the at least one sensor networked with the first mobile device.

6. The method of claim 1, further comprising synchronizing, by the sync server, the user sensory profile associated with the first user with the sensory information received from the first mobile device, wherein the remote information provided by the sync server to the second mobile device is used to determine whether to terminate a telecommunication session with the first mobile device before the first mobile device enters into the telecommunication session.

7. A sync server of a network comprising:

a processor; and a memory that stores instructions that, when executed by the processor, cause the processor to perform operations comprising:

establishing a sensory communication session between a first mobile device associated with a first user and a second mobile device associated with a second user, wherein the sensory communication session comprises a first connection between the sync server and the first mobile device and a second connection between the sync server and the second mobile device, and wherein the first user is associated with a first personal user environment comprising the first mobile device and at least one sensor networked with the first mobile device, and wherein the second user is associated with a second personal user environment comprising the second mobile device and at least one sensor networked with the second mobile device, discovering the at least one sensor networked with the first mobile device, configuring the sensory communication session to support the at least one sensor networked with the first mobile device, receiving, via the first connection of the sensory communication session between the sync server and the first mobile device, sensory information from the first mobile device, wherein the sensory information comprises data received from the at least one sensor networked with the first mobile device, generating, using the sensory information received from the first mobile device, historical sensory data associated with the first user, and data from a user sensory profile associated with the first user, remote information, wherein the remote information comprises at least a portion of the sensory information received from the first mobile device, wherein the remote information further comprises an avatar display generated by the sync server and an avatar environment generated by the sync server, and wherein the avatar display represents the first user and the avatar environment represents the first personal user environment associated with the first user, and providing, via the second connection of the sensory communication session between the sync server and the second mobile device without the first mobile device and the second mobile device directly interfacing with one another, the remote information comprising at least the portion of the sensory information received from the first mobile device, the avatar display generated by the sync server, and the avatar environment generated by the sync server to the second mobile device for presentation by the second mobile device.

8. The sync server of claim 7, wherein the first mobile device uses a remote sensory application programming interface to provide the sensory information to the sync server.

9. The sync server of claim 7, wherein the data received from the at least one sensor networked with the first mobile device comprises location information indicative of at least one of a speed, a direction, or an estimated travel time associated with the first mobile device.

10. The sync server of claim 7, wherein the sensory information includes tag values comprising time-stamped values determined by the at least one sensor networked with the first mobile device.

11. The sync server of claim 7, wherein the operations further comprise:
synchronizing the user sensory profile associated with the first user with the sensory information received from the first mobile device; and
recording the sensory information to the historical sensory data associated with the first user.

12. The sync server of claim 7, wherein the operations further comprise estimating a current state of the first user based, at least in part, upon the historical sensory data associated with the first user, wherein the historical sensory data associated with the first user is identified based, at least in part, upon the sensory information received from the first mobile device.

13. The sync server of claim 7, wherein the remote information provided to the second mobile device is used to determine whether to terminate a telecommunication session with the first mobile device before the first mobile device enters into the telecommunication session.

14. The sync server of claim 7, wherein the data received from the at least one sensor networked with the first mobile device comprises environmental information indicative of a current ambient condition at a location of the first mobile device, wherein the current ambient condition at the location of the first user comprises at least one of lighting conditions, temperature, pressure, or noise levels.

15. A non-transitory computer readable medium storing instructions that, when executed by a processor of a sync server, cause the processor to perform operations comprising:
establishing a sensory communication session between a first mobile device associated with a first user and a second mobile device associated with a second user, wherein the sensory communication session comprises a first connection between the sync server and the first mobile device and a second connection between the sync server and the second mobile device, and wherein the first user is associated with a first personal user environment comprising the first mobile device and at least one sensor networked with the first mobile device, and wherein the second user is associated with a second personal user environment comprising the second mobile device and at least one sensor networked with the second mobile device;
discovering the at least one sensor networked with the first mobile device;
configuring the sensory communication session to support the at least one sensor networked with the first mobile device;
receiving, via the first connection of the sensory communication session between the sync server and the first mobile device, sensory information from the first mobile device, wherein the sensory information comprises data received from the at least one sensor networked with the first mobile device;
generating, using the sensory information received from the first mobile device, historical sensory data associated with the first user, and data from a user sensory profile associated with the first user, remote information, wherein the remote information comprises at least a portion of the sensory information received from the first mobile device, wherein the remote information further comprises an avatar display generated by the sync server and an avatar environment generated by the sync server, and wherein the avatar display represents the first user and the avatar environment represents the first personal user environment associated with the first user; and
providing, via the second connection of the sensory communication session, between the sync server and the second mobile device without the first mobile device and the second mobile device directly interfacing with one another, the remote information comprising at least the portion of the sensory information received from the first mobile device, the avatar display generated by the sync server, and the avatar environment generated by the sync server to the second mobile device for presentation by the second mobile device.

16. The non-transitory computer readable medium of claim 15, wherein the operations further comprise:
synchronizing the user sensory profile associated with the first user with the sensory information received from the first mobile device; and
recording the sensory information received from the first mobile device to the historical sensory data associated with the first user.

17. The non-transitory computer readable medium of claim 15, wherein the remote information provided to the second mobile device is used to determine whether to terminate a telecommunication session with the first mobile device before the first mobile device enters into the telecommunication session.

18. The non-transitory computer readable medium of claim 15, wherein the operations further comprise estimating future sensory information for the first mobile device.

* * * * *